(12) United States Patent
Still et al.

(10) Patent No.: US 6,566,382 B2
(45) Date of Patent: May 20, 2003

(54) STABILIZED ISOTHIAZOLONE-CONTAINING COMPOSITIONS

(75) Inventors: Miron Gerard Still, Richmond, VA (US); Wan Pyo Hong, Whasung-gun (KR); Jin Man Kim, Suwon-si (KR); Ki Seung Choi, Euiwhang-si (KR); Jung Ho Park, Suwon-si (KR); Jae Min Ha, Suwon-si (KR); Hi Weon Jung, Suwon-si (KR); Soon Jong Hahn, Seoul (KR)

(73) Assignees: Lonza Inc., Fair Lawn, NJ (US); SK Chemicals Co., Ltd., Seoul (KR)

( * ) Notice: Subject to any disclaimer, the term of this patent is extended or adjusted under 35 U.S.C. 154(b) by 0 days.

(21) Appl. No.: 09/995,267

(22) Filed: Nov. 27, 2001

(65) Prior Publication Data

US 2003/0004198 A1 Jan. 2, 2003

(30) Foreign Application Priority Data

May 8, 2001 (KR) .................................... 2001-0024988

(51) Int. Cl.$^7$ .............................................. A01N 43/80
(52) U.S. Cl. ...................................... 514/372; 548/213
(58) Field of Search .......................... 514/372; 548/213

(56) References Cited

U.S. PATENT DOCUMENTS 5,910,503 A * 6/1999 Mattox et al. .............. 514/372

* cited by examiner

Primary Examiner—Laura L. Stockton
(74) Attorney, Agent, or Firm—Darby & Darby

(57) ABSTRACT

The present invention relates to isothiazolone-containing compositions comprising a) 3-isothiazolone compounds; b) a metal nitrate; c) magnesium chloride; d) at least one compound selected from the group consisting of iodic acid, periodic acid, an iodate salt, and a periodate salt; e) chlorite salts; and f) solvents. The invention further provides a method for stabilizing isothiazolone-containing compositions by inhibiting precipitation of by-products formed during production and precipitation of the compounds formed during storage. The compositions of the invention are useful for suppressing the growth of microorganisms.

11 Claims, No Drawings

STABILIZED ISOTHIAZOLONE-CONTAINING COMPOSITIONS

This application claims priority of Korean Patent Application No. 2001-0024988, filed on May 8, 2001, the content of which is incorporated herein by reference.

BACKGROUND OF THE INVENTION

1. Field of the Invention

The present invention relates to isothiazolone-containing compositions and a method for stabilizing them.

2. Description of the Related Art

Isothiazolones are compounds having wide-ranging sterilizing activity against many harmful organisms derived from animals and plants such as bacteria, fungi, algae, etc. Isothiazolones are added to products such as cosmetics and paints to inhibit the growth of harmful microorganisms in these products.

3-Isothiazolones decompose readily in polar organic solvents such as alcohol or water, and lose their biological activity with the lapse of time. Typically, a metal nitrate, such as magnesium nitrate, is added to most commercially available 3-isothiazolone-containing compositions to stabilize the 3-isothiazolones; such isothiazolone-containing compositions typically contain 1 to 20% by weight of isothiazolones and 15 to 25% by weight of the metal nitrate. A method for the prevention of chemical decomposition of 3-isothiazolones by adding a metal nitrite, a metal nitrate, etc., is disclosed in U.S. Pat. No. 3,870,795.

Although using metal nitrates as stabilizers of 3-isothiazolones preserves their sterilizing activity for longer periods of time, traces of precipitates are formed from the decomposition of 3-isothiazolone in solution during storage. The trace amounts of precipitates do not deleteriously impact the biological efficacy of isothiazolones; however, the presence of the precipitates gives an undesirable appearance to products, which is detrimental from a commercial standpoint.

In another method, Japanese Patent Publication No. 02-304005 discloses compositions containing 0.1 to 15% by weight of isothiazolones, 1 to 5000 ppm of copper ion, non-ion surfactant and organic solvents, but no nitrate salts. Japanese Patent Laid-open No. 05-170608 discloses that the use of bromic acid, iodic acid, periodic acid, iodates, and periodates instead of bivalent metal salts with magnesium nitrate as a stabilizer for isothiazolone-containing compositions can also prevent "salt shock" which often occurs when a metal nitrate is added to aqueous dispersions of polymers.

U.S. Pat. No. 5,910,503 discloses that a mixture of 0.5 to 35% by weight of isothiazolone compounds and 2 to 30% by weight of metal nitrate with 0.01 to 35% by weight of bromic acid, iodic acid, periodic acid, or salts thereof inhibits precipitation formed during storage and stabilizes aqueous dispersion of polymers (coagulation of latexes). However, in the method as above-mentioned, the amounts of bromic acid, iodic acid, periodic acid, or salts thereof used for preventing precipitate formation is very large. These large amounts thicken the compositions and, in addition, raise the cost of production of the compositions, making it economically unfeasible to employ these compositions commercially.

SUMMARY OF THE INVENTION

The present invention provides stabilized isothiazolone-containing compositions comprising two different stabilizers that can efficiently suppress precipitate formed by by-products in the compositions and formed upon storage of the compositions.

The present invention also provides a method for stabilizing isothiazolones by suppressing the generation of precipitates in isothiazolone-containing compositions.

To achieve the above objects and others, the present invention provides an isothiazolone-containing composition comprising:

a) a 3-isothiazolone compound having the structure of the formula:

Formula I

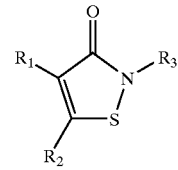

wherein:

$R_1$ and $R_2$ are the same or different, and each is hydrogen, a halogen, a $C_1$–$C_4$ alkyl group, or an aryl group in which $R_1$ and $R_2$ are cyclized, and $R_3$ is hydrogen, a $C_1$–$C_{18}$ alkyl group, a $C_2$–$C_{18}$ alkenyl group, a $C_2$–$C_{18}$ alkynyl group, a $C_3$–$C_{12}$ cycloalkyl group having a ring of 3–8 angles, a $C_{10}$–$C_{24}$ aralkyl group, or a $C_{10}$–$C_{24}$ aryl group;

b) a metal nitrate;

c) magnesium chloride;

d) at least one of the iodine-containing compounds selected from the group consisting of iodic acid, periodic acid, an iodate salt and a periodate salt;

e) a chlorite salt; and f) a solvent.

The present invention also provides a method for stabilizing isothiazolones comprising the steps of:

I) adding to a solvent
   a) 0.1 to 20% by weight of an 3-isothiazolone compound of the formula:

Formula I

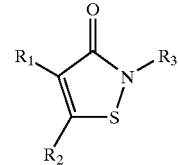

wherein:

$R_1$ and $R_2$ are the same or different, and each is hydrogen, a halogen, a $C_1$–$C_4$ alkyl group, or an aryl group in which $R_1$ and $R_2$ are cyclized, and $R_3$ is hydrogen, a $C_1$–$C_{18}$ alkyl group, a $C_2$–$C_{18}$ alkenyl group, a $C_2$–$C_{18}$ alkynyl group, a $C_3$–$C_{12}$ cycloalkyl group having a ring of 3–8 angles, a $C_{10}$–$C_{24}$ aralkyl group, or a $C_{10}$–$C_{10}$–$C_{24}$ aryl group;

(b) 0.1 to 25% by weight of a metal nitrate; and (c) 0.1 to 9.0% by weight of a magnesium chloride to form a solution; and II) mixing (d) 0.0001 to 0.01% by weight of at least one of the iodine-containing compounds selected from the group consisting of iodic acid, periodic acid, an iodate salt; and a periodate salt with (e) 0.0001 to 10% by weight of a chlorite salts to form a mixture; and III) combining the mixture of II) with the solution of I).

The present invention further provides a method of suppressing the growth of microorganisms comprising introducing a 3-isothiazolone-containing composition as described above into the habitat of microorganisms.

DETAILED DESCRIPTION OF THE PREFERRED EMBODIMENTS

The mixing of the two types of compounds, i.e., the iodine-containing compounds and the chlorite salts defined above, each having different reaction mechanisms, with magnesium chloride in specified concentrations, inhibits or prevents precipitate formation in compositions containing isothiazolones. By using concentrations even lower than those previously disclosed, the precipitation of by-products generated in the production of the compositions and minute precipitates formed by the compounds generated during storage can be significantly reduced or prevented, thereby effectively stabilizing the isothiazolone.

According to the present invention, preferred examples of the isothiazolone compounds of Formula 1 are 5-chloro-2-methyl-4-isothiazoline-3-one; 2-methyl-4-isothiazoline-3-one, 4,5-dichloro-2-methyl-4-isothiazoline-3-one; 5-chloro-2-n-octyl-3-isothiazolone; 4,5-dichloro-2-n-octyl-3-isothiazolone and benzisothiazolone. Alternatively, a mixture of these compounds may be used, preferably, of 5-chloro-2-methyl-4-isothiazoline-3-one and 2-methyl-4-isothiazoline-3-one, wherein the weight ratio is preferably from 1:20 to 20:1.

In the isothiazolone-containing compositions of the present invention, the isothiazolones of Formula I are used in an amount that is typically used in isothiazolone-containing solutions, namely, from 0.1 to 20% by weight of the isothiazolone.

To reduce or inhibit the degradation of isothiazolones, the composition of the present invention comprises from 0.1 to 25% by weight of metal nitrate. Preferred metal nitrates include lithium nitrate, potassium nitrate, magnesium nitrate, calcium nitrate, and ammonium nitrate. Most preferred is magnesium nitrate.

Furthermore, the composition of the present invention preferably includes from 0.1 to 9% by weight of magnesium chloride to suppress the formation of the isothiazolone precipitate. Magnesium chloride in an amount of less than 0.1 wt % may not effectively inhibit precipitation; when present in an amount of more than 9 wt %, it may itself precipitate due to its limited solubility.

The composition of the present invention further includes at least one of the iodine-containing compounds defined above in an amount of from about 0.0001 to 0.01 wt %, preferably from 0.001 to 0.005 wt %. If less than 0.0001 wt % is used, precipitation may not be effectively inhibited; an amount above 0.01 wt % is not preferred in commercial applications since it increases the cost without any attendant benefit.

The composition of the invention preferably includes chlorite salts to suppress precipitate formation. The amount of chlorite salts used is preferably from about 0.0001 to 10 wt %, more preferably from 0.0001 to 0.1 wt %. If less than 0.0001 wt % is used, it may not be effective in preventing precipitation; an amount above 10 wt % is not preferred in commercial applications due to the increased cost. The chlorite salts are preferably sodium chlorite, potassium chlorite, and mixtures thereof.

The isothiazolone compounds are stabilized by using the chlorite salts together with at least one iodine-containing compound, most preferably in a weight ratio of the iodine-containing compounds to the chlorite salts of from 0.001:0.005 to 0.0001:0.05. Preferred iodine-containing compounds include lithium iodate, sodium iodate, potassium iodate, ammonium iodate, lithium periodate, sodium periodate, potassium periodate, and ammonium periodate. Most preferred are iodic acid, periodate dihydrate, potassium iodate, and sodium iodate.

The composition of the invention further comprises at least one solvent. Preferred solvents include water, ethylene glycol, propylene glycol, dipropylene glycol, polypropylene glycol, diethylene glycol, triethylene glycol, 1.5-pentanediol, 2,4-pentanediol, benzyl alcohol, and mixtures thereof.

The method of the present invention for preparing isothiazolone-containing compositions comprises adding 3-isothiazolone compounds of Formula I, a metal nitrate, and a magnesium chloride to a solvent to prepare a mixed solution. Then at least one of the iodine-containing compounds is mixed with a chlorite salt. The resultant mixture is added to the solution containing 3-isothiazolone prepared in the foregoing step.

The present invention further provides a method for suppressing the growth of microorganisms derived from animals and plants, for example, bacteria, fungi and algae. According to the present invention, the growth of microorganisms may be inhibited or the microorganisms may be killed. The isothiazolone-containing compositions of the invention may be introduced into the habitats of any microorganisms, including cooling towers, air washers, boilers, mineral slurries, wastewater treatments, ornamental fountains, reverse osmosis filtration systems, ultrafiltration systems, ballast water, evaporative condensers, heat exchangers, pulp and paper processing fluids, plastics, emulsions and dispersions, paints, latexes, coating agents and metal working fluids.

To better define the present invention, the following Examples are set forth. These Examples are only to better the understanding of the invention, but are not intended to limit its scope.

EXAMPLES

Examples 1 and 2

The content of the 3-isothiazolone compositions of Examples 1 and 2 are shown below in Table 1. 3-Isothiazolone compounds were prepared by using an approximate 3:1 mixture of 5-chloro-2-methyl-4-isothiazoline-3-one (CMI) and 2-methyl-4-isothiazoline-3-one (MI). The compositions of Examples 1 and 2 were prepared by mixing 3-isothiazolone compounds, magnesium nitrate, magnesium chloride, and water, followed by adding $KIO_3$ (Example 1 only) and 25% $NaClO_2$, $HIO_4 \cdot 2H_2O$ (Example 2 only) and 25% $NaClO_2$, respectively, for preventing precipitation.

The isothiazolone compositions of Comparative Examples 1 to 4 having the content shown below in Table 1 were prepared as described above. Each isothiazolone-containing solution was stored in an oven at 65° C. for 92 days, then analyzed by HPLC to determine the percentage of CMI remaining in the compositions. The results are shown below in Table 2.

TABLE 1

| Sample | CMI + MI | Mg(NO₃)₂ | MgCl₂ | KIO₃ | HIO₄·2H₂O | 25% NaClO₂ | Water |
|---|---|---|---|---|---|---|---|
| Comparative Example 1 | 14.7 | 17.4 | 4.1 | — | — | — | 63.8 |
| Comparative Example 2 | 14.7 | 17.4 | 4.1 | 0.005 | — | — | 63.79 |
| Comparative Example 3 | 14.7 | 17.4 | 4.1 | — | — | 0.2 | 63.6 |
| Comparative Example 4 | 11.7 | 17.4 | — | 0.005 | — | 0.2 | 70.69 |
| Example 1 | 14.7 | 17.4 | 4.1 | 0.005 | — | 0.2 | 63.59 |
| Example 2 | 14.7 | 17.4 | 4.1 | — | 0.0005 | 0.2 | 63.59 |

TABLE 2

| | Initial | | | | After 92 days, at 65° C. | | | | |
|---|---|---|---|---|---|---|---|---|---|
| Wt % | MI | CMI | CMI + MI | CMI/MI ratio | MI | CMI | CMI + MI | CMI/MI ratio | Precipitation |
| Comparative Example 1 | 3.9 | 10.8 | 14.7 | 2.76 | 3.6 | 8.5 | 12.1 | 2.36 | Yes |
| Comparative Example 2 | 3.9 | 10.8 | 14.7 | 2.76 | 3.7 | 9.3 | 13.0 | 2.51 | Yes |
| Comparative Example 3 | 3.9 | 10.8 | 14.7 | 2.76 | 3.6 | 8.6 | 12.2 | 2.38 | Yes |
| Comparative Example 4 | 1.0 | 10.7 | 11.7 | 10.4 | 0.9 | 7.5 | 8.4 | 8.6 | Yes |
| Example 1 | 3.9 | 10.8 | 14.7 | 2.76 | 3.9 | 10.7 | 14.6 | 2.72 | No |
| Example 2 | 3.9 | 10.8 | 14.7 | 2.76 | 3.9 | 10.7 | 14.6 | 2.72 | No |

The data in Table 2 show that, for the compositions of Comparative Examples 1 to 4, after storage for 92 days at 65° C., the concentration of major constituents and the ratio of CMI/MI decreased, and precipitates were formed in all solutions. In contrast, in the compositions of Examples 1 and 2, even after storage for 92 days at 65° C., the concentration of major constituents barely dropped and the ratio of CMI/MI remained high. Furthermore, no precipitate was formed in either solution, indicating that isothiazolone-containing solutions were stabilized.

Experimental Example

The number of insoluble particulates existing in compositions of Comparative Examples 1 to 3 and Examples 1 and 2 was determined when the samples were prepared, and several times during sample storage at ambient temperature. The counting of insoluble particulates was conducted by using Liquidborne Particle Counter System (Model: Cl-1000, manufactured by Climet Co.) at 10.0 ml/min of flow rate, 2.0 ml of tare volume, calculating the total number of insoluble particulates more than 1 μm, per 10.0 ml of isothiazolone-containing solutions. The results are reported below in Table 3.

TABLE 3

| Storage days | Comparative Example 1 | Comparative Example 2 | Comparative Example 3 | Example 1 | Example 2 |
|---|---|---|---|---|---|
| 0 | 952 | 967 | 985 | 993 | 997 |
| 18 | 98,980 | 13,130 | 18,534 | 1,879 | 1,987 |
| 22 | 148,372 | 100,471 | 137,932 | 4,982 | 5,207 |

The data in Table 3 indicates that in Comparative Examples 1 to 3 the number of insoluble particulates increased rapidly during the first 18 days and continued to increase until the 22nd day, thereby generating large amounts of precipitates. In contrast, in the compositions of Examples 1 and 2, the number of insoluble particulate increased slightly over the first 18 days and remained relatively small even after 22 days. Thus, the generation of precipitates was restrained.

What is claimed is:

1. A composition, comprising:
   a) a 3-isothiazolone compound of the formula

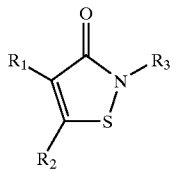

wherein:
   $R_1$ and $R_2$ are the same or different, each is hydrogen, a halogen a $C_1$–$C_4$ alkyl group, or an aryl group in which $R_1$ and $R_2$ are cyclized; and R<sub>3</sub> is hydrogen, a $C_1$–$C_{18}$ alkyl group, a $C_2$–$C_{18}$ alkenyl group, a $C_2$–$C_{18}$ alkynyl group, a $C_3$–$C_{12}$ cycloalkyl group having a ring of 3–8 angles, a $C_{10}$–$C_{24}$ aralkyl group, or a $C_{10}$–$C_{24}$ aryl group;
b) a metal nitrate;
c) magnesium chloride;
d) at least one of the iodine-containing compounds selected from the group consisting of iodic acid, periodic acid, an iodate salt, and a periodate salt;
e) a chlorite salt; and
f) a solvent.

2. The composition according to claim 1, comprising:
a) 0.1 to 20 wt % of the 3-isothiazolone compound;
b) 0.1 to 25 wt % of the metal nitrate;
c) 0.1 to 9.0 wt % of magnesium chloride;
d) 0.0001 to 0.01 wt % of at least one of the iodine-containing compounds selected from the group consisting of iodic acid, periodic acid, an iodate salt, and a periodate salt;
e) 0.0001 to 10 wt % of the chlorite salt.

3. The composition according to claim 2, comprising 0.001 to 0.005 wt % of at least one of the compounds selected from the group consisting of iodic acid, periodic acid, an iodate salt, and a periodate salt; and 0.0001 to 0.1 wt % of the chlorite salt.

4. The composition according to claim 2, comprising 0.001 to 0.005 wt % of at least one of the compounds selected from the group consisting of iodic acid, periodic acid, an iodate salt, and a periodate salt; and 0.0001 to 0.05 wt % of the chlorite salt.

5. The composition according to claim 1, wherein the 3-isothiazolone compound is selected from at least one of the compounds of the group consisting of 5-chloro-2-methyl-4-isothiazoline-3-one; 2-methyl-4-isothiazoline-3-one; 4,5-dichloro-2-methyl-4-isothiazoline-3-one; 5-chloro-2-n-octyl-3-isothiazolone; 4,5-dichloro-2-n-octyl-3-isothiazolone; and benzisothiazolone.

6. The composition according to claim 1, wherein the metal nitrate is selected from at least one of the compounds selected from the group consisting of lithium nitrate, potassium nitrate, magnesium nitrate, calcium nitrate, and ammonium nitrate.

7. The composition according to claim 1, wherein the iodine-containing compound d) is at least one of the compounds selected from the group consisting of lithium iodate, sodium iodate, potassium iodate, ammonium iodate, lithium periodate, sodium periodate, potassium periodate, ammonium periodate, iodic acid, periodate dihydrate, potassium iodate, and sodium iodate.

8. The composition according to claim 1, wherein the chlorite salt is at least one of the compounds selected from the group consisting of sodium chlorite and potassium chlorite.

9. The composition according to claim 1, wherein the solvent is at least one of the compounds selected from the group consisting of water, ethylene glycol, propylene glycol, dipropylene glycol, polypropylene glycol, diethylene glycol, triethylene glycol, 1.5-pentanediol, 2,4-pentanediol and benzylalcohol.

10. A method for stabilizing an isothiazolone comprising:
I.) adding to solvent
i) 0.1 to 20% by weight of 3-isothiazolone compounds of the formula

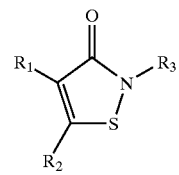

wherein:

R<sub>1</sub> and R<sub>2</sub> are the same or different, each is hydrogen, a halogen, a $C_1$–$C_4$ alkyl group, or an aryl group in which R<sub>1</sub> and R<sub>2</sub> are cyclized; and R<sub>3</sub> is hydrogen, a $C_1$–$C_{18}$ alkyl group, a $C_2$–$C_{18}$ alkenyl group, a $C_2$–$C_{18}$ alkynyl group, a $C_3$–$C_{12}$ cycloalkyl group having a ring of 3–8 angles, a $C_{10}$–$C_{24}$ aralkyl group, or a $C_{10}$–$C_{24}$ aryl group;
(b) 0.1 to 25% by weight of a metal nitrate; and
(c) 0.1 to 9.0% by weight of magnesium chloride to form a solution; and II) mixing
(d) 0.0001 to 0.01% by weight of at least one of the iodine-containing compounds selected from the group consisting of iodic acid, periodic acid, an iodate salt; and a periodate salt with
(e) 0.0001 to 10% by weight of a chlorite salts to form a mixture; and III) combining the mixture of II) with the solution of I).

11. The method for stabilizing an isothiazolone according to claim 10, wherein the 3-isothiazolone compound is at least one of the compounds selected from the group consisting of 5-chloro-2-methyl-4-isothiazoline-3-one; 2-methyl-4-isothiazoline-3-one; 4,5,-dichloro-2-methyl-4-isothiazoline-3-one; 5-chloro-2-n-octyl-3-isothiazolone; 4,5-dichloro-2-n-octyl-3-isothiazolone; and benzisothiazolone.

* * * * *